United States Patent [19]

Alikhan et al.

[11] Patent Number: 5,006,116
[45] Date of Patent: Apr. 9, 1991

[54] TAMPON WITH SINGLE LAYER POWDER BONDED WRAP

[75] Inventors: Mir I. Alikhan, Marietta, Ga.; Sandra M. Colrud, Appleton, Wis.; James C. Sneyd, Marietta, Ga.

[73] Assignee: Kimberly-Clark Corporation, Neenah, Wis.

[21] Appl. No.: 287,790

[22] Filed: Dec. 21, 1988

[51] Int. Cl.⁵ .................. A61F 13/15; A61F 13/20
[52] U.S. Cl. ................... 604/365; 604/367; 604/366; 604/370; 604/372; 604/374; 604/378; 604/904
[58] Field of Search ................. 604/11–18, 604/285–287, 365–367, 370, 374, 372, 378–380, 904

[56] References Cited

U.S. PATENT DOCUMENTS

| | | | |
|---|---|---|---|
| 3,683,912 | 8/1972 | Olson et al. | 604/904 |
| 4,050,463 | 9/1977 | Schaar | 604/366 |
| 4,056,103 | 11/1977 | Kaczmarzyk | 128/285 |
| 4,222,381 | 9/1980 | Widlund et al. | 128/270 |
| 4,305,391 | 12/1981 | Jackson | 128/270 |
| 4,335,722 | 6/1982 | Jackson | 128/285 |
| 4,391,869 | 7/1983 | Cook et al. | 428/218 |
| 4,537,590 | 8/1985 | Pieniak | 604/379 |
| 4,551,143 | 11/1985 | Cook et al. | 604/371 |
| 4,857,065 | 8/1989 | Seal | 604/368 |

FOREIGN PATENT DOCUMENTS 0269380  6/1988  European Pat. Off. .
2061339  5/1981  United Kingdom ............... 604/370

Primary Examiner—Ronald Frinks
Assistant Examiner—Stephanie L. Iantorno
Attorney, Agent, or Firm—Patrick C. Wilson

[57] ABSTRACT

A tampon having a single layer wrap of fibers attached together by a powder binder. The wrap is embossed around a tampon pledget. The wrap in one embodiment includes a blend of hydrophobic synthetic fibers and hydrophilic cellulosic fibers laminated together with bonding powder. Another embodiment has only hydrophilic cellulosic fibers laminated together with bonding powder.

23 Claims, 3 Drawing Sheets

Fig_2

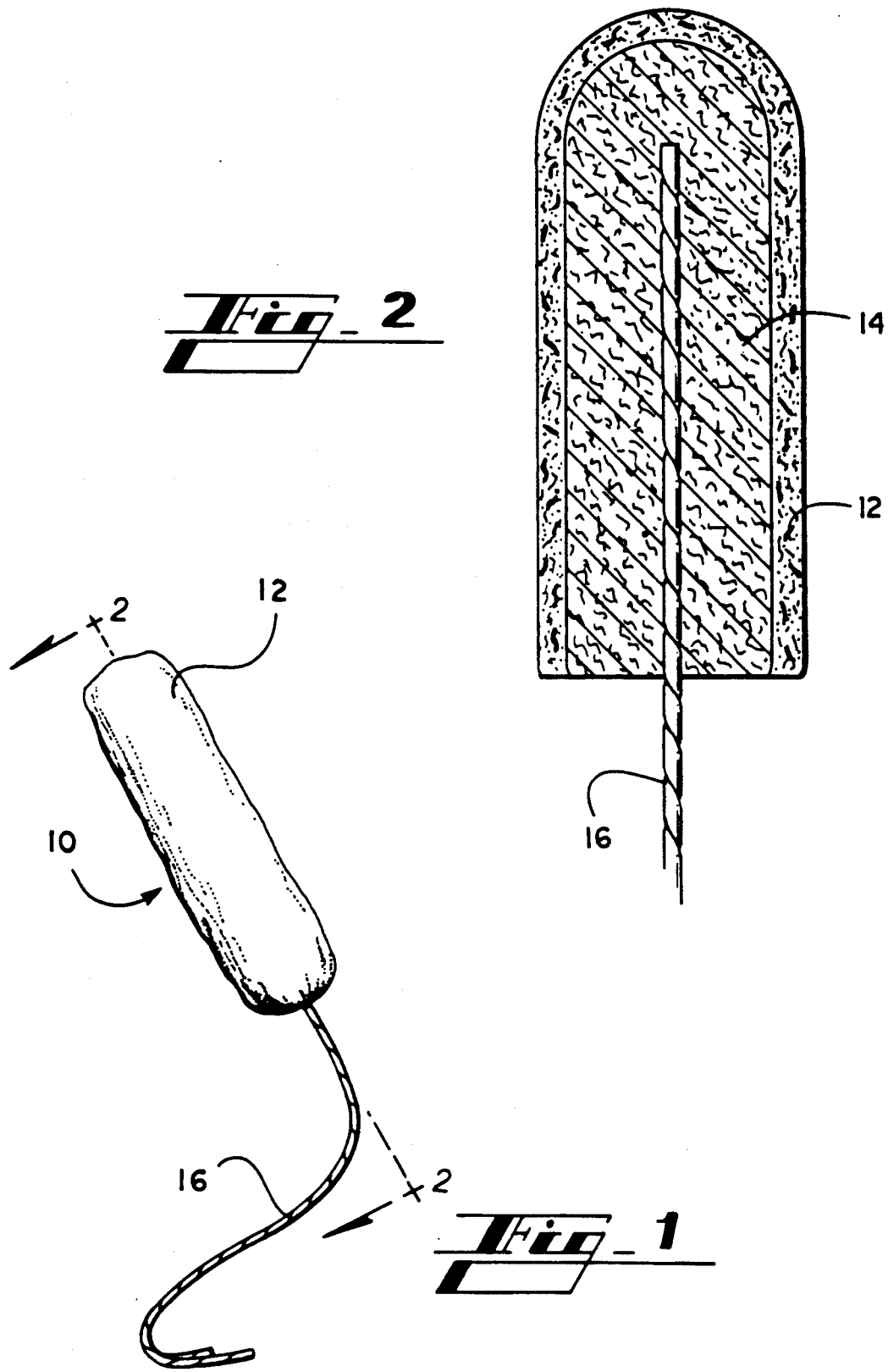

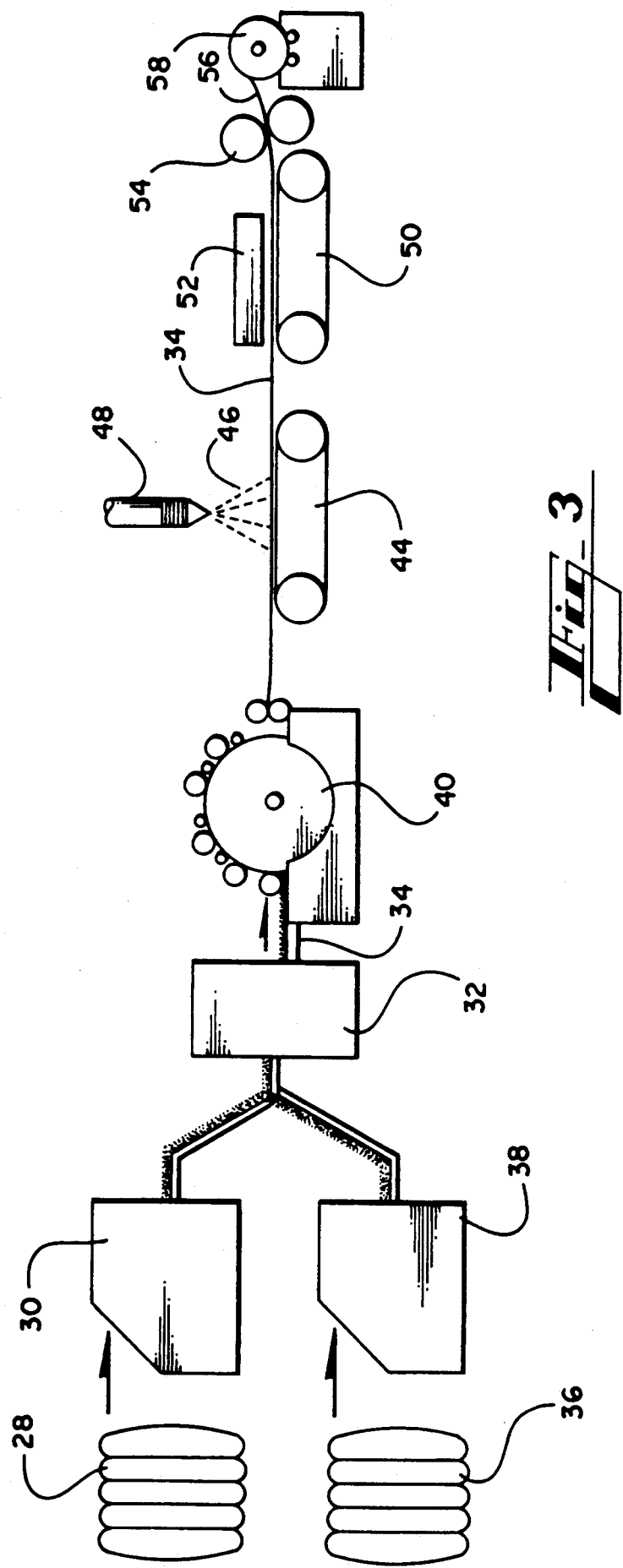

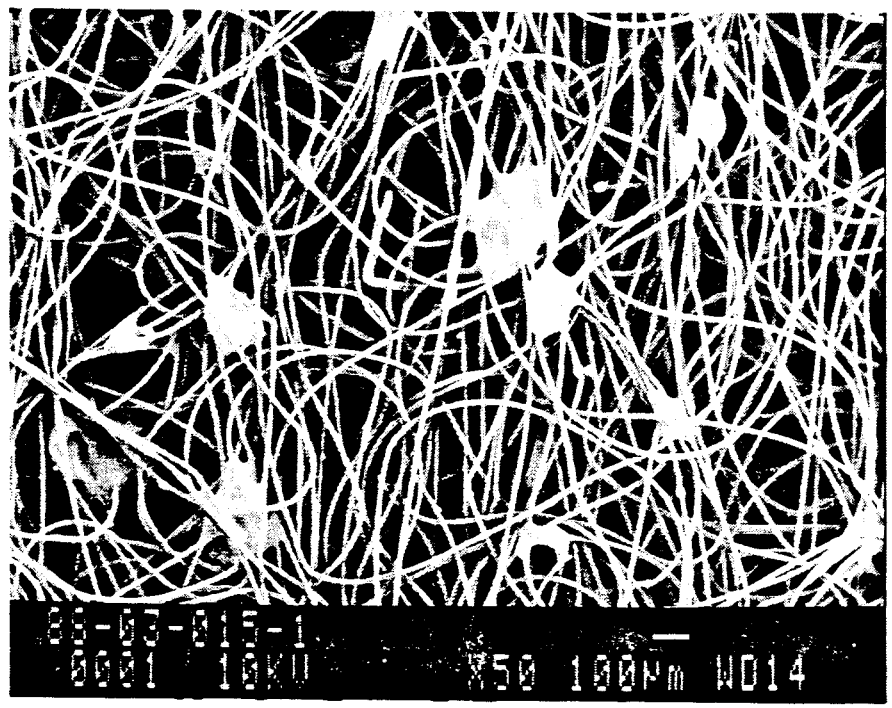
Fig_4

TAMPON WITH SINGLE LAYER POWDER BONDED WRAP

TECHNICAL FIELD

The present invention relates to an improved tampon having a single layer wrap. More particularly, the present invention relates to an improved tampon wrapped by a web of powder bonded fibers, including homogeneous blends of hydrophobic and hydrophilic fibers, as well as blends of hydrophilic fibers.

BACKGROUND OF THE INVENTION

Presently available tampons consist of an inner absorbent core covered by a fluid permeable wrap. The wrap permits fluid to enter the tampon but restrains fluid flow from the tampon. The wraps are made from a variety of fibers, including blended natural and synthetic fibers. For instance, U.S. Pat. No. 4,056,103 describes a wrap made from a blend of cotton, rayon, polyester, and superabsorbent fibers.

The fibers for the web material used as the wrap are generally non-woven. The fibers are held together in the web by either a resin bond or a pressure/temperature-set fuse bond. U.S. Pat. No. 4,305,391 describes a tampon having an absorbent core with two fluid permeable wraps. The inner wrap is partially fluid absorbent to aid in minimizing withdrawal forces and to aid in the prevention of reverse flow. The pore size of the outer wrap is greater than that of the inner wrap to facilitate rapid passage of fluid. The outer wrap is preferably of a lower loft and basis weight than the inner wrap when superabsorbent fibers are employed. Suitable inner wrap fibers are described as meltblown polyolefins, meltblown polyolefin-pulp mixture and polyesters. Suitable outer wrap fibers are spunbonded polyolefins, polyesters, and the like. The inner wrap is laid directly on the outer wrap and heated to fuse in random the contact areas between the two layers of material.

Resin bonding fibers to form the web fabric is described in U.S. Pat. Nos. 4,391,869 and 4,551,143. The non-woven, air-laid fabric is formed predominantly of textile length, synthetic, resilient fibers of staple length. The references describe the bonding solution characteristics as providing less than 180 percent solution pickup and more than 15 percent dry solids add-on.

There are problems, however, with resin bonding and heat fuse bonding of fibers for tampon wraps. These problems include additional manufacturing requirements to evaporate the moisture from the web and unsatisfactory resin performance in sealing the web. Heat fusing thermoplastic fibers also presents problems, including insufficient fusing of fibers as well as overfusing of fibers. Insufficient fusing results in a weak web while overfusing results in a stiff web. These methods of bonding also limit tampon production processing because the web material separates or pulls apart at high processing speed.

An improved tampon is needed with a powder bonded wrap that permits rapid manufacture of tampons having a high absorbance capacity and a lower probability of leakage.

SUMMARY OF THE INVENTION

The improved tampon of the present invention provides a single layer homogeneous blend of fibers powder bonded to form a web for a wrap to cover a tampon pledget. Generally described, the tampon wrap includes blended fibers laminated together with bonding powder. In an alternate embodiment, the web includes hydrophobic fibers blended with hydrophilic fibers and laminated together with bonding powder. The hydrophobic fibers aid insertion and withdrawal of the tampon during low menstrual flow while the hydrophilic fibers promote radial wicking. Yet another alternative embodiment would have a wrap made of 100 percent cellulosic fibers glued together with bonding powder.

More particularly, the tampon wrap is comprised of a blend of fibers, such as polyester fibers and cellulosic fibers. Bonding powder glues adjacent fibers together at various contact points. Preferably, the bonding powder comprises approximately 15 to 30 percent of the fabric web by weight, although the bonding powder could be as low as about 7 percent or as high as approximately 35 percent by weight.

It is therefore an object of the present invention to provide a personal care absorbent article with a single layer powder bonded wrap.

It is an object of the present invention to provide a personal care absorbant article having a single layer wrap of fibers glued together with bonding powder.

It is an object of the present invention to provide a personal care absorbent article with a single layer powder bonded tampon wrap including hydrophobic fibers and hydrophilic fibers.

It is also an object of the present invention to provide a tampon with a wrap having fibers glued together with bonding powder.

It is also an object of the present invention to provide a single layer tampon wrap that is permits a tampon to be easily inserted and withdrawn on low flow days but also has a high absorbance capacity.

It is also an object of the present invention to provide a single layer tampon wrap that permits a tampon to be easily inserted and withdrawn on low flow days and also has a reduced probability of leakage.

It is also an object of the present invention to provide a single layer powder bonded wrap that is easily manufactured.

It is another object of the present invention to provide a tampon wrap which can be used in a high speed process to manufacture tampons.

Other objects, features and advantages of the present invention will become apparent upon reading the following detailed description and upon reference to the drawings.

BRIEF DESCRIPTION OF THE DRAWINGS

FIG. 1 is a perspective view of the improved tampon of the present invention.

FIG. 2 is a cross-sectional view of the tampon of FIG. 1, taken along line 2—2 of FIG. 1.

FIG. 3 is a schematic diagram showing the process for making the improved tampon of the present invention.

FIG. 4 is an electron microscope photograph of an embodiment of the web wrap for the tampon illustrated in FIG. 1.

DETAILED DESCRIPTION OF THE PREFERRED EMBODIMENTS

Referring now in more detail to the drawings, in which like numerals refer to like parts throughout the several views, FIG. 1 shows an assembled tampon 10 for personal care, including a single layer powder bonded wrap 12 embodying the present invention. As shown in FIG. 2, the preferred embodiment of the tampon 10 includes a tampon wrap 12 having a homogeneous blend of fibers. The fibers are laminated together with bonding powder. In one alternate embodiment the fibers are 100 percent cellulosic while yet another embodiment has a homogenous blend of hydrophobic and hydrophilic synthetic and natural fibers. It is noted that thermally-fuseable synthetic fibers, if present in the particular blend, may also contribute to the lamination, depending on the heating temperatures used during manufacture. The wrap 12 is radially wrapped or embossed onto a conventional, absorbant core or pledget 14. Embodiments which include up to about 10 percent thermoplastic fiber content reduce the amount of powder bond required in the outer layer and facilitate bonding between the wrap and the pledget. Withdrawal means such as a removal string 16 is compressed within the absorbant core by means well known in the art.

The tampon wrap 12 is composed of a homogeneous mixture of carded fibers bonded with bonding powder. Preferably, the hydrophobic fibers are synthetic fibers such as polyester, polypropylene or polyethylene. In one embodiment, the fibers are Celanese TM Fortrel TM Polyester Type 300 fibers, having a length of less than about 3.8 centimeters. The basic weight of the hydrophobic fibers preferably ranges from approximately 7 $g/m^2$ to approximately 12 $g/m^2$.

The hydrophilic fibers preferably are composed of a mixture of carded cellulosic fibers, such as rayon, cotton, and the like. The cellulosic fibers have a length of between approximately 2.5 and 5 centimeters. The cellulosic fibers in an alternate embodiment uses only rayon, such as Avtex rayon fibers, having a length of less than about 3.8 centimeters. As with the hydrophobic fibers, the basic weight of the hydrophobic fibers preferably ranges from approximately 7 $g/m^2$ to approximately 12 $g/m^2$.

Appropriate thermoplastic powder bonding material is available from various manufacturers, including Eastobond ® FA-252 powder manufactured by Eastman Chemical Products, Inc. (Kingsport, Tenn.) and EMS-Chemi Grilon powder 1284. The bonding powder preferably comprises approximately 15 to 30 percent of the total weight of the wrap 12, although in alternate embodiments would be as low as about 7 percent or as high as about 35 percent, by weight.

Embodiments of the present invention in which the hydrophilic fibers comprise greater than 50 percent of the tampon wrap by weight would have enhanced radial wicking. An alternate embodiment however has only cellulosic hydrophilic fibers such as only rayon fibers.

FIG. 3 illustrates a procedure for manufacturing the wrap 12 for the tampon 10 of the present invention. The wrap 12 as discussed here includes a homogeneous blend of hydrophobic and hydrophilic fibers. One of skill in the art will appreciate that this procedure would be similar for a wrap having only hydrophobic or only hydrophilic fibers. The staple hydrophobic fibers 28 which comprise a portion of the tampon wrap 12 are placed into a fiber opener-feeder 30 to separate the clumps of staple fibers into individual fibers for carding. The hydrophobic fibers 28 are fed out of the opener-feeder 30 into a blending machine 32.

The staple hydrophilic fibers 36 that will comprise a portion of the tampon wrap 12 are placed into a second fiber opener-feeder 38 to separate the clumps of staple fibers 36 into individual fibers for carding. As with the hydrophobic fibers 28, the separated hydrophilic fibers 36 are fed out of the second opener-feeder 38 into the fiber blender 32. The blender 32 makes a homogeneous blend 34 of the hydrophobic fibers and the hydrophilic fibers. The blended fibers 34 are fed to a carding machine 40 which combs the fibers 34 to align the carded fibers axially. The aligned hydrophobic and hydrophilic fibers 34 are layered on the open mesh conveyor belt 44. In an alternate embodiment the blended fibers would be removed from the carding machine 40 in a random alignment. Preferably the open mesh conveyor belt 44 moves at a speed of between approximately 15 to 22 meters.

Opening the fibers may be a multi-step process to avoid or reduce fiber breakage or damage which may occur with a one-pass opening process. Thus, additional fiber opener apparatus such as openers 30 and 38 may preceed or succeed the blending process using the blender 32. After a final fine opening, the fibers pass through an air duct (not illustrated) to a chute feed (not illustrated) at the back of the carding machine 40. The chute feed uniformly feeds fibers to the carding machine 40 across the width of the card.

The bonding powder 46 is sprayed onto the layered hydrophobic and hydrophilic aligned fibers 34 with a conventional dry spraying unit 48. The flow rate of the bonding powder 46 is preferably adjusted so that the weight of the bonding powder added to the fibers is between approximately 7 to 35 percent by weight. For a typical tampon wrap having a basis weight between 14 $g/m^2$ and 22 $g/m^2$, the powder weight is between approximately 1 and 8 $g/m^2$. The bonding powder affects both the strength of the web and its softness. Higher amounts of powder increases web strength, but decreases web softness. Lower amounts of powder permit the web to have increased softness but decreased strength. If the weight of the powder is too low, then the web will have insufficient strength to permit proper handling by automated machinery. Increased amounts of powder may be cost prohibitive because the powder is relatively expensive compared with the fibers. Also, a web with a high percentage by weight of bonding powder may be too stiff to provide satisfactory performance. FIG. 4 illustrates an embodiment of the present invention viewed under an electron microscope. The powder binder appears as discrete spots glueing the fibers together. The binder melts and coats the adjacent fibers with a non-uniform discontinuous layer. Any bonding powder 46 that falls through the combed fibers 34 and the open mesh conveyor belt 44 is collected beneath the conveyor belt and is recycled back to the power spray unit 48. Appropriate thermoplastic powder binders include the Eastman FA-252 as discussed above, the EMS-Chemi Grilon powder 1284, or similar such powder binders.

The mixture of aligned fibers 34 and the bonding powder 46 is transferred onto a Teflon ® coated conveyor belt 50 and the belt is passed under an infrared heater 52 to soften or melt the bonding powder 46. The speed of the Teflon ® coated conveyor belt 50 is preferably slightly faster than the speed of the open mesh conveyor belt 44. Preferably, the temperature of the infrared heater 52 is approximately 104° to 116° C. Preferably the melting point of the bonding powder 46 is lower than the melting point of the fibers 34 so that the bonding powder 46 will soften or melt to bond the fibers 34 to one another.

The heated fiber web of bonded fibers 34 are passed between a pair of nip rolls 54 to compress the hydrophobic and hydrophilic fibers into a laminated layer 56 with the fibers 34 bonded together with the adhesive bonding powder. Preferably, the nip rolls 54 are heated to a temperature of between approximately 71° to 93° C. and have a rotational speed of between approximately 18 to 25 meters per minute so that the speed of the nip rolls 54 is slightly faster than the speed of the conveyor belt 44. Preferably the pressure of the nip rolls 54 is between approximately 16 and 19.6 kilograms per linear centimeter. Again, the temperature setting is dependent on the line speed, the web density and fiber type. Higher temperatures in the bonding process would cause the synthetic fibers to partially melt and fuse together, thereby increasing the bonding of the web fibers. In an alternate embodiment, the compressed, laminated layer 56 passes through a second heater (not shown) and pair of nip rolls (not shown) heated at a lower temperature than the first pair of nip rolls 54. The cooled, compressed, laminated layer 56 forms the homogeneous blend, powder bond wrap 12 which is wound at a rate of approximately 20.1 m/min around a winder or spool 58 for storage.

When needed, an appropriate amount of the single layer wrap 12 is cut from the spool 58 and is thermally bonded, such as by embossing, onto an absorbant core or pledget 14. The powder bonded wrap 12 permits assembly of the tampon at processing speeds in excess of those used with resin or thermal bonded wraps. The pledget 14 is preferably made of an absorbant material such as cellulose fibers, including rayon and cotton. The core includes conventional withdrawal means 16, such as a removal string, compressed within the core 14.

The wrap 12 is made of resilient materials that promote expansion when wetted to further enhance the surface area exposed to the menstrual fluid and thus increase the absorbance capacity of the tampon. Expansion of the tampon 10 also causes the formation of an effective barrier to menstrual flow out of the vagina, further preventing premature failure or leakage.

The following specific examples will illustrate the invention as it applies in particular to a method of manufacturing a single layer homogeneous powder bonded wrap of the present invention. It will be appreciated that other examples will be apparent to those skilled in the art and that the invention is not limited to these specific illustrative examples.

EXAMPLE I

An embodiment of the single layer powder bond wrap of the present application would be reduced to practice by following the manufacturing steps recited below.

Hydrophobic Celanese Fortrel type 300 polyester fibers, 1.5 denier × 3.8 centimeters staple length, (Celanese Fibers Operations, Charlotte, N.C.) are loaded into one of the fiber opener-feeders.

A blended hydrophilic mixture of rayon and cotton is loaded into the remaining fiber opener-feeder. The rayon fibers are autex rayon, regular 1.5 denier × 3.8 centimeters. The cotton fibers are natural and unbleached with a length of approximately 1.25 inches. The rayon is 80 percent of the hydrophilic fibers by weight.

Both the separated hydrophobic and hydrophilic staple fibers are fed out of each respective fiber opener-feeder into a carding machine. The carding machine is a roller top carding machine made by Soco-Lowell and has a forty inch width.

The aligned blend of hydrophobic and hydrophilic fibers exit the carding machine onto an open mesh conveyor belt moving at 18.3 m/min so that the longitudinal axis of the aligned fibers is parallel to the direction of movement of the conveyor belt.

The total fiber weight of the rayon, cotton and polyester in this example is 13 g/m$^2$ with the polyester fibers comprising 70 percent and the cellulosic fibers comprising 30 percent by weight.

Bonding powder is sprayed onto the blended fiber layer with a conventional dry spraying unit at an appropriate rate so that the amount of bonding powder applied is 3.3 g/m$^2$. This provides approximately 20 percent by weight bonding powder. The bonding powder is Eastobond® FA-252 Hot Melt adhesive powder, medium grade.

The fiber-bonding powder mixture is transferred to a Teflon® coated conveyor belt moving at 19.2 m/min. The belt is passed under an infrared heater having a surface temperature of 110° C.

The bonded fibers are rolled between a pair of heated nip rolls to compress the layers. The nip rolls are heated at a temperature of 87.8° C.

The bonded mixture is passed under a second infrared heater and a second pair of nip rolls having a temperature of 76.7° C. The speed of the conveyor is 20.1 m/min as it passes under the second infrared heater.

The compressed, blended fibers are thus laminated to form the single layer wrap and the wrap is then wound around a winder at a speed of 20.1 m/min.

EXAMPLE II

The method of manufacture of Example I is utilized with the following exception:
The total fiber weight of the rayon, cotton and polyester in this example is 17.5 g/m$^2$. The amount of powder added to the fiber is 4 g/m$^2$.

EXAMPLE III

The method of manufacture of Example I is utilized with the following exception:
The total fiber weight of the rayon, cotton and polyester in this example is 15.6 g/m$^2$. The amount of powder added to the fiber is 3.5 g/m$^2$.

EXAMPLE IV

The method of manufacture of Example I is utilized to manufacture a single ply hydrophilic web of 100 percent rayon. The total fiber weight for the web is 14 to 14.5 g/m$^2$ with an additive of 2.7 g/m$^2$ of bonding powder.

The following powder bonded rayon wraps would be similarly manufactured:

| Rayon Fiber Basis Weight (g/m$^2$) | Bonding Powder (g/m$^2$) | Powder Percent |
| --- | --- | --- |
| 14.9 | 2.75 | 15 |
| 13.7 | 3.6 | 20 |
| 14.6 | 4.1 | 22 |

EXAMPLE V

The method of manufacture of Example I is utilized to manufacture a homogeneous blend of 60 percent polypropylene fibers and 40 percent rayon fibers by weight. Three alternate embodiments with differing amounts of bonding powder are described below.

| Base Fiber Weight (g/m²) | Bonding Powder (g/m²) | Powder Percent |
|---|---|---|
| 16.38 | 1.15 | 7 |
| 16.38 | 1.64 | 10 |
| 16.38 | 2.29 | 14 |

While this invention has been described in detail with particular reference to a preferred embodiment thereof, it will be understood that variations and modifications can be made without departing from the spirit and the scope of the invention as described herein and as defined in the appended claims.

What is claimed is:

1. A personal care absorbent article, comprising:
   an absorbent pledget; and
   a single layer powder bonded wrap embossed onto the absorbent pledget, the wrap comprising a homogeneous blend of hydrophobic fibers and hydrophilic fibers laminated together with bonding powder.

2. The personal care absorbent article as recited in claim 1, wherein the hydrophobic fibers are polyester fibers; and
   wherein the hydrophilic fibers are cellulosic fibers.

3. The personal care absorbent article of claim 1, wherein the hydrophilic fibers comprise more than 50 percent of the wrap by weight.

4. The personal care absorbent article as recited in claim 3, wherein the bonding powder comprises approximately 7 to 35 percent of the wrap by weight.

5. The personal care absorbent article as recited in claim 1, further comprising removal means attached to said absorbent pledget for removing said absorbent article.

6. The personal care absorbent article of claim 1, wherein said absorbent pledget is made primarily of cellulosic fibers.

7. The personal care absorbent article of claim 1, wherein the bonding powder comprises approximately 7 to 35 percent of the wrap by weight.

8. A personal care absorbent article comprising:
   an absorbant pledget:
   means attached to said absorbant pledget for removing said personal care absorbent article from the human body; and
   a single layer powder bonded wrap covering said absorbant pledget, the wrap comprising a homogeneous blend of hydrophobic fibers and hydrophilic fibers laminated together with an adhesive bonding powder.

9. The personal care absorbent article as recited in claim 8 wherein the bonding powder is heat-set.

10. The personal care absorbent article of claim 8, wherein the absorbent pledget is made of cotton.

11. The personal care absorbent article of claim 8, wherein the hydrophobic fibers are polyester fibers; and wherein the hydrophilic fibers are cellulosic fibers.

12. The personal care absorbent article of claim 11, wherein said bonding powder comprises approximately 7 to 35 percent of the wrap by weight.

13. The personal care absorbent article of claim 8, wherein the hydrophilic fibers comprise more than 50 percent of the wrap by weight.

14. The personal care absorbent article of claim 13, wherein the bonding powder comprises between approximately 7 and 35 percent of the wrap by weight.

15. An improved tampon comprising:
   (a) an absorbant pledget;
   (b) withdrawl means compressed within said absorbant pledget for withdrawing said tampon from the human body;
   (c) a single layer tampon wrap of fibers laminated together with a powder binder and embossed onto said absorbant pledget, said wrap including a homogeneous blend of hydrophobic fibers laminated to hydrophilic fibers by the powder binder.

16. The improved tampon of claim 1, wherein the wrap is comprised of rayon fibers and a powder bond material, whereby the powder melts under heat to connect the fibers together randomly.

17. The tampon of claim 1, wherein the absorbant pledget is made of cotton.

18. The tampon of claim 1, wherein the hydrophobic fibers are polyester fibers.

19. The tampon of claim 18, wherein said bonding powder comprises approximately 7 to 35 percent of the wrap by weight.

20. The tampon of claim 1, wherein the hydrophilic fibers are cellulosic fibers.

21. The tampon of claim 20, wherein said bonding powder comprises approximately 7 to 35 percent of the wrap by weight.

22. The tampon of claim 15, wherein the hydrophilic fibers comprise more than 50 percent of the tampon wrap by weight.

23. The tampon of claim 22, wherein the bonding powder comprises approximately 7 to 35 percent of the wrap by weight.

* * * * *